US00PP28035P3

(12) United States Plant Patent

Hagiwara et al.

(10) Patent No.: US PP28,035 P3

(45) Date of Patent: May 16, 2017

(54) *CALIBRACHOA* PLANT NAMED 'INTA 06575'

(50) Latin Name: *Calibrachoa hybrida*
Varietal Denomination: INTA 06575

(71) Applicants: Juan Carlos Hagiwara, Buenos Aires (AR); Maria Julia Pannunzio, Buenos Aires (AR); Gabriela Rosa Facciuto, Ituzaingo (AR)

(72) Inventors: Juan Carlos Hagiwara, Buenos Aires (AR); Maria Julia Pannunzio, Buenos Aires (AR); Gabriela Rosa Facciuto, Ituzaingo (AR)

(73) Assignee: Instituto Nacional de Tecnologia Agropecuaria "INTA", Buenos Aires (AR)

( * ) Notice: Subject to any disclaimer, the term of this patent is extended or adjusted under 35 U.S.C. 154(b) by 0 days.

(21) Appl. No.: 14/756,432

(22) Filed: Sep. 4, 2015

(65) Prior Publication Data

US 2017/0071116 P1 Mar. 9, 2017

(51) Int. Cl.
*A01H 5/02* (2006.01)

(52) U.S. Cl.
USPC ..... Plt./413

(58) Field of Classification Search
USPC ..... Plt./413
See application file for complete search history.

(56) References Cited

PUBLICATIONS

PLUTO Plant Variety Database Aug. 10, 2016. p. 1.*

* cited by examiner

*Primary Examiner* — Annette Para
(74) *Attorney, Agent, or Firm* — C. A. Whealy

(57) ABSTRACT

A new and distinct *Calibrachoa* plant named 'INTA 06575', characterized by its compact, upright to outwardly spreading and mounding to eventually trailing plant habit; vigorous growth habit; freely branching habit; dense and bushy appearance; early and freely flowering habit; purple-colored flowers with yellow-colored throats; and good garden performance.

1 Drawing Sheet

Botanical designation: *Calibrachoa caesia*×*Calibrachoa hybrida.*

Cultivar denomination: 'INTA 06575'.

BACKGROUND OF THE INVENTION

The present invention relates to a new and distinct cultivar of *Calibrachoa* plant, botanically known as *Calibrachoa caesia*×*Calibrachoa hybrida* and hereinafter referred to by the name 'INTA 06575'.

The new *Calibrachoa* plant is a product of a planned breeding program conducted by the Inventors in Hurlingham, Province of Buenos Aires, Argentina. The objective of the breeding program is to create new vigorous and freely-flowering *Calibrachoa* plants with unique and attractive flower coloration and good garden and summer performance.

The new *Calibrachoa* plant originated from a cross-pollination conducted by the Inventors in Hurlingham, Province of Buenos Aires, Argentina in September, 2005 of a proprietary selection of *Calibrachoa caesia* identified as code number 2003092512, not patented, as the female, or seed, parent with the proprietary selection of *Calibrachoa hybrida* referred to as 'Dark Blue', not patented, as the male, or pollen, parent. The new *Calibrachoa* plant was discovered and selected by the Inventors as a single flowering plant within the progeny of the stated cross-pollination in a controlled greenhouse environment in Hurlingham, Province of Buenos Aires, Argentina in October, 2006.

Asexual reproduction of the new *Calibrachoa* plant by vegetative terminal cuttings in a controlled greenhouse environment in Hurlingham, Province of Buenos Aires, Argentina since October, 2006 has shown that the unique features of this new *Calibrachoa* plant are stable and reproduced true to type in successive generations.

SUMMARY OF THE INVENTION

Plants of the new *Calibrachoa* have not been observed under all possible combinations of environmental conditions and cultural practices. The phenotype may vary somewhat with variations in environmental conditions such as temperature and light intensity without, however, any variance in genotype.

The following traits have been repeatedly observed and are determined to be the unique characteristics of 'INTA 06575'. These characteristics in combination distinguish 'INTA 06575' as a new and distinct *Calibrachoa* plant:

1. Compact, upright to outwardly spreading and mounding to eventually trailing plant habit.
2. Vigorous growth habit.
3 Freely branching habit; dense and bushy appearance.
4. Early and freely flowering habit.
5. Purple-colored flowers with yellow-colored throats.
6. Good garden performance.

The new *Calibrachoa* plant can be compared to plants of the female parent selection. Plants of the new *Calibrachoa* differ primarily from plants of the female parent selection in the following characteristics:

1. Plants of the new *Calibrachoa* are more outwardly spreading than and not as upright as plants of the female parent selection.
2. Plants of the new *Calibrachoa* have smaller leaves than plants of the female parent selection.
3. Plants of the new *Calibrachoa* have larger flowers than plants of the female parent selection.

The new *Calibrachoa* plant can be compared to plants of the male parent selection. Plants of the new *Calibrachoa* differ primarily from plants of the male parent selection in the following characteristics:

1. Plants of the new *Calibrachoa* are taller than plants of the male parent selection.
2. Plants of the new *Calibrachoa* have longer internodes than plants of the male parent selection.
3. Plants of the new *Calibrachoa* and the male parent selection differ slightly in flower color as plants of the male parent selection have purple violet-colored flowers.
4. Plants of the new *Calibrachoa* have better garden performance than plants of the male parent selection.

Plants of the new *Calibrachoa* can be compared to plants of the *Calibrachoa* sp. 'USCALI11', disclosed in U.S. Plant Pat. No. 14,968. In side-by-side comparisons conducted in Bonsall, Calif., plants of the new *Calibrachoa* differed primarily from plants of 'USCALI11' in the following characteristics:

1. Plants of the new *Calibrachoa* were shorter than plants of 'USCALI11'.
2. Plants of the new *Calibrachoa* were more vigorous than plants of 'USCALI11'.
3. Plants of the new *Calibrachoa* had smaller flowers than plants of 'USCALI11'.
4. Plants of the new *Calibrachoa* and 'USCALI11' differed in flower color as plants of 'USCALI11' had light red purple-colored flowers.

Plants of the new *Calibrachoa* can also be compared to plants of the *Calibrachoa* sp. 'Caltrapi', not patented. In side-by-side comparisons conducted in Bonsall, Calif., plants of the new *Calibrachoa* differed primarily from plants of 'Caltrapi' in the following characteristics:

1. Plants of the new *Calibrachoa* were more mounding than and not as flat as plants of 'Caltrapi'.
2. Plants of the new *Calibrachoa* were more vigorous than plants of 'Caltrapi'.
3. Plants of the new *Calibrachoa* had smaller flowers than plants of 'Caltrapi'.

BRIEF DESCRIPTION OF THE PHOTOGRAPHS

The accompanying colored photographs illustrate the overall appearance of the new *Calibrachoa* plant showing the colors as true as it is reasonably possible to obtain in colored reproductions of this type. Colors in the photographs may differ slightly from the color values cited in the detailed botanical description which accurately describe the colors of the new *Calibrachoa* plant.

The photograph at the bottom of the sheet is a side perspective view of a typical flowering plant of 'INTA 06575' grown in a container.

The photograph at the top of the sheet is a close-up view of a typical flowering plant of 'INTA 06575'.

DETAILED BOTANICAL DESCRIPTION

The aforementioned photographs and following observations, measurements and values describe plants grown during the summer in 10-cm containers in an outdoor nursery in Bonsall, Calif. During the production of the plants, day temperatures averaged 27° C., night temperatures averaged 18° C. and light levels ranged from 7,000 to 10,000 foot-candles. Plants were pinched two times and were six weeks old when the photographs and description were taken. In the following description, color references are made to The Royal Horticultural Society Colour Chart, 2007 Edition, except where general terms of ordinary dictionary significance are used.

Botanical classification: *Calibrachoa caesia*×*Calibrachoa hybrida* 'INTA 06575'.

Parentage:

*Female, or seed, parent*.—Proprietary selection of *Calibrachoa caesia* identified as code number 2003092512, not patented.

*Male, or pollen, parent*.—Proprietary selection of *Calibrachoa hybrida* referred to as 'Dark Blue', not patented.

Propagation:

*Type*.—By vegetative terminal cuttings.

*Time to initiate roots, summer*.—About five to seven days at temperatures ranging from 20° C. to 30° C.

*Time to initiate roots, winter*.—About seven to ten days at temperatures ranging from 15° C. to 25° C.

*Time to produce a rooted plant, summer*.—About 21 to 25 days at temperatures ranging from 20° C. to 30° C.

*Time to produce a rooted plant, winter*.—About 23 to 28 days at temperatures ranging from 15° C. to 25° C.

*Root description*.—Medium in thickness, fibrous; typically white in color, actual color of the roots is dependent on substrate composition, water quality, fertilizer type and formulation, substrate temperature and physiological age of roots.

*Rooting habit*.—Freely branching; medium density.

Plant description:

*Plant and growth habit*.—Compact, upright to outwardly spreading and mounding to eventually trailing plant habit; freely branching habit with about five primary lateral branches each with about four to six secondary branches; pinching enhances branching; dense and bushy appearance; vigorous growth habit.

*Plant height*.—About 7.5 cm.

*Plant diameter*.—About 23 cm.

Lateral branch description:

*Length*.—About 13 cm.

*Diameter*.—About 2 mm.

*Internode length*.—About 1.6 cm.

*Strength*.—Strong.

*Aspect*.—Initially upright then outwardly spreading to eventually trailing.

*Texture*.—Pubescent; minute.

*Color*.—Close to 144A.

Leaf description:

*Arrangement*.—Before flowering, alternate; after flowering, opposite; leaves simple.

*Length*.—About 2.7 cm.

*Width*.—About 1 cm.

*Shape*.—Elliptical.

*Apex*.—Rounded.

*Base*.—Attenuate.

*Margin*.—Entire.

*Texture, upper and lower surfaces*.—Pubescent; minute.

*Luster, upper and lower surfaces*.—Matte.

*Venation pattern*.—Pinnate; arcuate.

*Color*.—Developing leaves, upper and lower surfaces: Close to 146B. Fully expanded leaves, upper surface: Close to 137B; venation, close to 147B. Fully expanded leaves, lower surface: Close to 147B; venation, close to 147C.

*Petioles*.—Length: About 6 mm. Diameter: About 1 mm. Strength: Strong, flexible. Texture, upper and lower surfaces: Pubescent; minute. Color, upper and lower surfaces: Close to 146C.

Flower description:

*Flower type and flowering habit*.—Single salverform flowers arising from leaf axils; freely flowering habit with typically about ten open flowers per lateral branch and more than 200 flower buds and open flowers per plant at a time; flowers face upright to outwardly.

*Fragrance*.—None detected.

*Natural flowering season*.—Plants of the new *Calibrachoa* begin flowering about four weeks after planting; plants flower continuously from the early spring though the summer until the autumn in Southern California.

*Flower longevity*.—Individual flowers last about five days on the plant depending on ambient temperature; flowers persistent.

*Flower buds*.—Length: About 1.8 cm. Diameter: About 5 mm. Shape: Oblong, elongate. Color: Close to 156C.

*Flower diameter*.—About 2.6 cm by 2.6 cm.

*Flower length* (*height*).—About 2.4 cm.

*Flower throat diameter*.—About 5 mm.

*Flower tube length*.—About 1.4 cm.

*Flower tube diameter, base*.—About 3 mm.

*Corolla*.—Arrangement: Five fused petals in a single whorl opening into a flared trumpet. Petal lobe length (from throat): About 1.1 cm. Petal lobe width: About 1.3 cm. Petal shape: Fan-shaped. Petal apex: Rounded, slightly and shallowly emarginate. Petal margin: Entire. Petal texture, upper surface: Smooth, glabrous; velvety. Petal texture, lower surface: Pubescent; minute and primarily along the veins. Throat texture: Smooth, glabrous. Tube texture: Pubescent; minute and primarily along the veins. Petal luster, upper and lower surfaces: Matte. Throat luster: Slightly shiny. Tube luster: Matte. Color: Petal lobe, when opening, upper surface: Close to N80A. Petal lobe, when opening, lower surface: Close to 201D. Petal lobe, fully opened, upper surface: Close to N78A; venation, close to 83A; with development, color becoming closer to N78B. Petal lobe, fully opened, lower surface: Close to 83D; venation, close to 83B to 83C. Throat: Close to 1B; venation, close to 186A. Tube: Close to 83B; venation, close to N79B.

*Calyx*.—Arrangement: One star-shaped calyx tube with five sepals fused towards the base and arranged in a single whorl. Sepal length: About 9 mm. Sepal width: About 2 mm. Sepal shape: Lanceolate. Sepal apex: Acute. Sepal margin: Entire. Sepal texture, upper and lower surfaces: Pubescent; minute. Sepal color, upper and lower surfaces: Close to 146A.

*Peduncles*.—Length: About 1.8 cm. Diameter: About 1 mm. Angle: About 45° from stem axis. Strength: Strong. Texture: Pubescent; minute. Color: Close to 145A.

*Reproductive organs*.—Stamens: Quantity: Five per flower. Filament length: About 9 mm. Filament color: Close to 145D. Anther length: About 1 mm. Anther shape: Oval. Anther color: Close to 8B. Pollen amount: Scarce. Pollen color: Close to 8B. Pistils: Quantity: One per flower. Pistil length: About 9 mm. Style length: About 7 mm. Style color: Close to 145C. Stigma shape: Round. Stigma color: Close to 144B. Ovary color: Close to 145B. Seeds and fruits: Seed and fruit development have not been observed on plants of the new *Calibrachoa*.

Garden performance: Plants of the new *Calibrachoa* have been observed to have good garden performance and tolerate wind, rain and temperatures ranging from about 1° C. to about 40° C.

Pathogen & pest resistance: Plants of the new *Calibrachoa* have not been observed to be resistant to pathogens and pests common to *Calibrachoa* plants.

It is claimed:

1. A new and distinct *Calibrachoa* plant named 'INTA 06575' as illustrated and described.

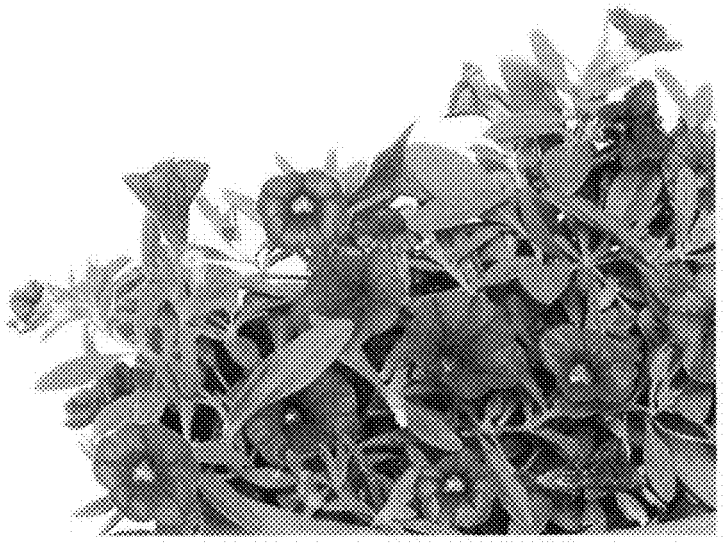
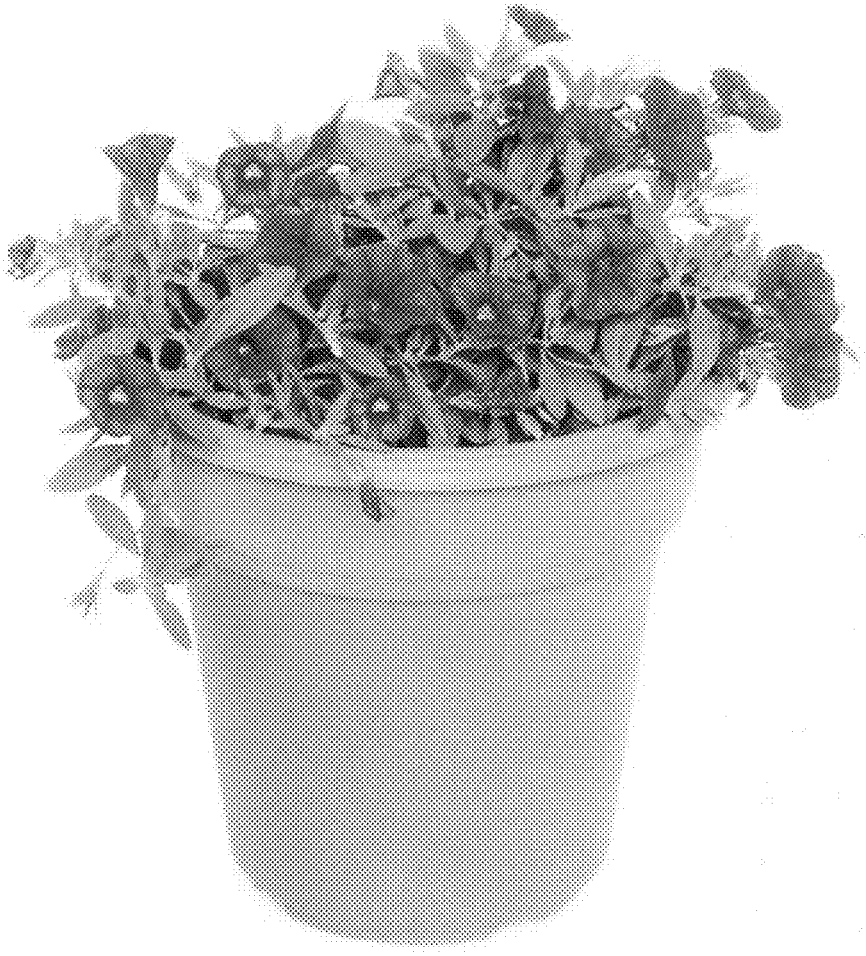

* * * * *